United States Patent
Ihalainen

(10) Patent No.: US 6,974,253 B2
(45) Date of Patent: Dec. 13, 2005

(54) CONNECTION BETWEEN X-RAY SENSOR AND HOLDER

(75) Inventor: Pekka Ihalainen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 10/822,634

(22) Filed: Apr. 12, 2004

(65) Prior Publication Data

US 2005/0226390 A1    Oct. 13, 2005

(51) Int. Cl.[7] ............................ A61B 6/14; G03B 42/04
(52) U.S. Cl. ....................... 378/191; 378/168; 378/170
(58) Field of Search ........................ 378/191, 168–170

(56) References Cited

U.S. PATENT DOCUMENTS

| | | | | |
|---|---|---|---|---|
| 1,453,194 A | * | 4/1923 | Shaw | 378/170 |
| 1,548,171 A | * | 8/1925 | Raper | 378/168 |
| 1,706,117 A | * | 3/1929 | Heckel | 378/170 |
| 2,392,109 A | * | 1/1946 | Vlock | 378/170 |
| 4,949,370 A | * | 8/1990 | Tanaka | 378/170 |
| 5,090,047 A | * | 2/1992 | Angotti et al. | 378/170 |
| 6,203,195 B1 | | 3/2001 | Willis | |
| 6,461,038 B2 | | 10/2002 | Pellegrini et al. | |
| 6,520,676 B1 | | 2/2003 | Schmitz | |

* cited by examiner

Primary Examiner—Craig E. Church
Assistant Examiner—Krystyna Suchecki
(74) Attorney, Agent, or Firm—Andrus, Sceales, Starke & Sawall, LLP

(57) ABSTRACT

In an arrangement for connecting a dental X-ray imaging sensor to a holder; the sensor (9) is a flat piece (11) having a planar radiation sensitive area, and at least one communication line (12) connected to said radiation sensitive area for data transfer; and the holder (8) is an elongated body having a first end provided with means for detachable connection of said sensor. The sensor has a peg (3) projecting from said flat piece. The peg is provided with a widened outer end and a neck between said outer end and said flat piece. Further, the neck has a configuration with a plurality of alternate larger diameters and smaller diameters. The holder has at its first end a fork (4) with a gap, which is adapted to fit onto said neck at least in two different positions. The interaction between the fork and the larger and smaller diameters of the neck prohibits unintended pivot of said sensor in respect to the holder.

18 Claims, 4 Drawing Sheets

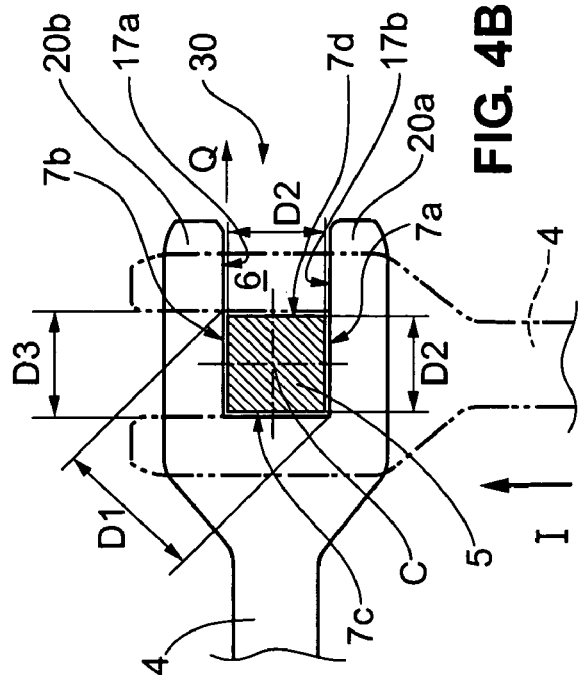
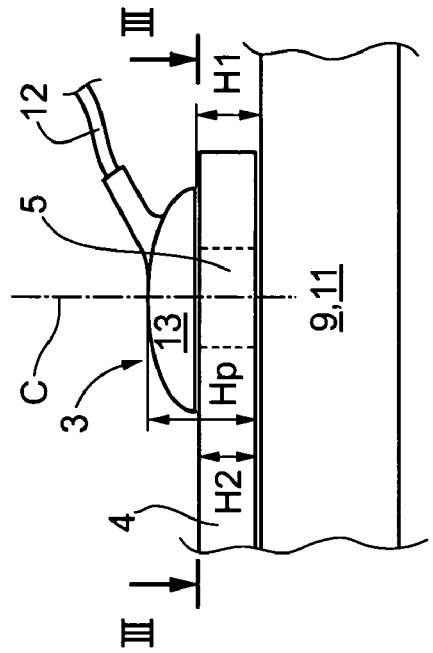
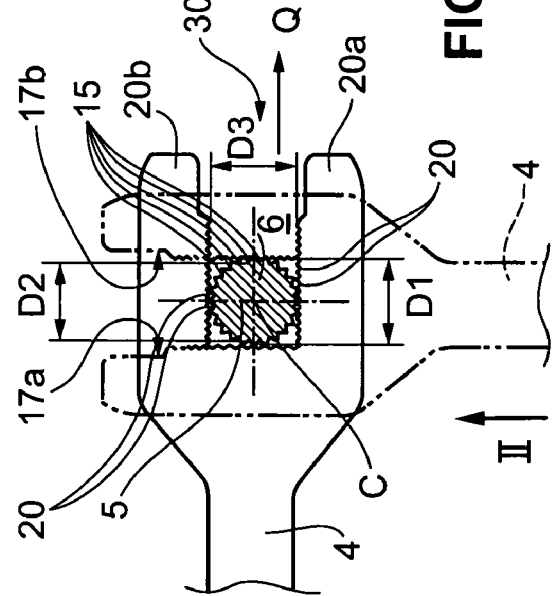
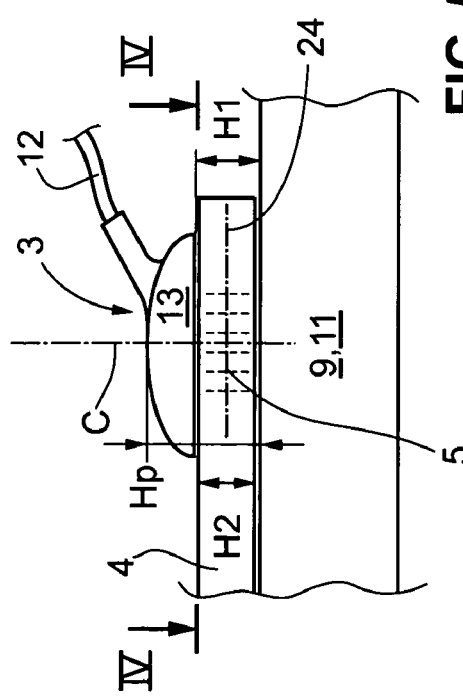

CONNECTION BETWEEN X-RAY SENSOR AND HOLDER

FIELD OF THE INVENTION

The invention relates an arrangement for connecting a substantially flat dental X-ray imaging sensor having a radiation sensitive area and provided with an image data communication line to an elongated holder.

BACKGROUND OF THE INVENTION

The most traditional way of positioning a flat dental X-ray imaging sensor in the mouth of the patient and against the patient's teeth is simply to put the separate sensor in the intended place, and ask the patient to keep it against his/hers teeth by his/hers finger. This procedure has been used both for the photographic film sensors and for the electronic imaging sensors. This procedure is simple and cheap, but attaining the correct place and position—e.g. tilt angle—is quite unreliable, as is keeping the sensor stationary during X-ray exposure. It is suggested several types of special holders, in which the electronic X-ray imaging sensor is attached, to overcome these problems.

The patent publication U.S. Pat. No. 6,203,195 B1 discloses a holder, which accommodates dental sensors of various dimensions for receiving X-rays and thereby transmitting signals showing the condition of a patient's teeth to a computer or other recorder. This holder is provided with a clasp engaging one edge of a sensor while adjustably movable to cause a fixed portion of the holder to engage the opposite edge of the sensor. Interfitting ratchet teeth on clasp and holder retain the parts in the required position, and a protruding handle portion and an arm portion are also provided for positioning the sensor within the teeth of the patient in the desired position. The publication also suggests the use of a different holder acting as a bite block for holding the patient's jaws apart in certain occasions. The sides of the bite blocks are non-parallel, thereby reducing the shadows of such sides on the X-ray usage. This kind of sensor holder is quite complicated rendering it expensive, and difficult to sterilize. Its use in practice is also very cumbersome. The sensor can be placed only in such position, in which the signal cables from the sensor are in the direction perpendicular to the elongated shank.

The patent publication U.S. Pat. No. 6,520,676 B1 discloses a holder used in dental radiography being substantially an ultra-thin bite wing with a reinforced juncture between the bite wing and the integral sleeve such that a perpendicular orientation is maintained while the sensor is in the patient's mouth. The dimensions of that invention allow the patient's teeth to be in close proximity while an image are formed using the sensor, and the disposable sensor provides a mechanism for indicating a previous use to ensure single use. The holder is formed using an injection molding process of polyethylene of 40 to 80 melt flow, with a preferred melt flow of 60. The thin bite wing is enabled because of a reinforced T-joint at the base of the sleeve along the spine connecting the bite wing, which maintains the sleeve and the holder in a perpendicular orientation with respect to the plane formed by the upper and lower surfaces of the mating teeth. This holder does not include any handle at all, but the sensor is kept in place by the bite wing positioned between the teeth. The bite wing here is not intended to hold the patient's jaws apart, accordingly being a contrary solution to the bite block according to U.S. Pat. No. 6,203,195 B1 mentioned above. The sensor can be placed only in such position, in which the signal cables from the sensor are in the direction parallel to the bite wing.

The patent publication U.S. Pat. No. 6,461,038 B2 discloses a holder for a dental X-ray image sensor that comprises a handle having a first end. The first end of the handle is connected to a first elastic loop. The first elastic loop holds the dental X-ray image sensor. As a result of the combination of a handle and an elastic loop, the X-ray image sensor may be placed in the mouth and its position adjusted depending upon the individual patient's palate and the area lateral to the patient's tongue. The handle can further comprise a second end that is connected to a second elastic loop. The second elastic loop can also hold a dental X-ray image sensor. In such an embodiment, the second elastic loop is arranged transversely in comparison to the first elastic loop. The handle is preferably elongated and flat with an upper side and a lower side. When the first elastic loop is formed from an elastic strip having a first end and a second end, the first end of the elastic strip is connected to the upper side of the handle while the second end of the elastic strip is being connected to the lower side of the handle thereby forming a loop that extends outward from an edge of the handle defined by the upper and lower sides of the handle. Alternatively, the first and second ends of the elastic loop may be disposed in and secured in the horizontal slot of the handle to thereby fasten the loop to the handle. The opening defined by the elastic loop can thus be parallel to the upper and lower sides of the handle, or normal to the upper and lower sides of the handle. In a further embodiment, the publication discloses a saddle, which includes a back wall having two opposing ends.

Each end of the back wall is connected to a bracket having a U-shaped configuration. The brackets are arranged in an opposing relationship to one another. The elastic loop extends around the back wall and between the U-shaped brackets to secure the saddle to the handle. The U-shaped brackets then accommodate a dental X-ray image sensor between the brackets with the loop extending between the sensor and the back wall. Contrary to the solutions according to U.S. Pat. No. 6,203,195 B1 and U.S. Pat. No. 6,520,676 B1 the sensor can be here placed in two positions perpendicular to each other, but in the opposite ends of the handle. As a drawback, there shall be different holders for sensors of different dimensions, because each size of the elastic loop operates reliably and without damaging the sensor only for sensors having specified dimensions.

SUMMARY OF THE INVENTION

An object of the invention is to obtain an arrangement for connecting a dental X-ray imaging sensor to a holder, which arrangement allows reliable and rapid attachment of the sensor in the holder prior its use for imaging, and rapid detachment of the sensor from the holder after use. Reliability means e.g. that the connection between the positions of the sensor relative to the holder stays unchanged during use. A further object of the invention is to obtain this kind of arrangement, which allows positioning of the sensor, with e.g. a longitudinal configuration, in at least two positions perpendicular to each other in the holder.

The problems described above can be overcome and the objects defined above can be reached by the arrangement for connecting a dental X-ray imaging sensor to a holder according to the invention. In the inventive arrangement: said sensor is a flat piece with a length and a width, a radiation sensitive area extending along said length and width, and at least one communication line is connected to said radiation sensitive area for data transfer; said holder is an elongated body having a first end provided with means for detachable connection of said sensor; a peg projects from said flat piece in a direction perpendicular to said length and width, said peg provided with a widened outer end and a neck between said outer end and said flat piece, said neck having a configuration with a plurality of alternate larger diameters and smaller diameters; and a fork with a gap is at said first end of the holder, said gap being adapted to fit onto said neck at least in two different positions, an interaction between said fork and said larger and smaller diameters of the neck prohibiting unintended pivot of said sensor in respect to the holder.

BRIEF DESCRIPTION OF THE DRAWINGS

The foregoing summary, and the following detailed description of the preferred embodiments of the present invention, will be better understood when read in conjunction with the accompanying drawings, in which:

FIGS. 4A and 4B represent the preferred first configuration of the neck of the peg in the sensor, seen from the side of the peg—direction I in FIGS. 1 to 3 and 4B, and in cross-sectional view perpendicular the length of the peg respectively, whereupon the fork has shown with continuous in a first alternative position and with phantom line in a second alternative position—section III—III in FIG. 4A.

FIGS. 5A and 5B represent the second configuration of the neck of the peg in the sensor, seen from the side of the peg—direction II in FIGS. 1 to 3 and 5B, and in cross-sectional view perpendicular the length of the peg respectively, whereupon the fork has shown with continuous in a first alternative position and with phantom line in a second alternative position—section IV—IV in FIG. 5A.

FIG. 6 shows the X-ray sensor seen from the radiated side thereof, in an axonometric view direction V in FIGS. 1 to 3.

DETAILED DESCRIPTION OF THE PREFERRED EMBODIMENTS

Figure 1:
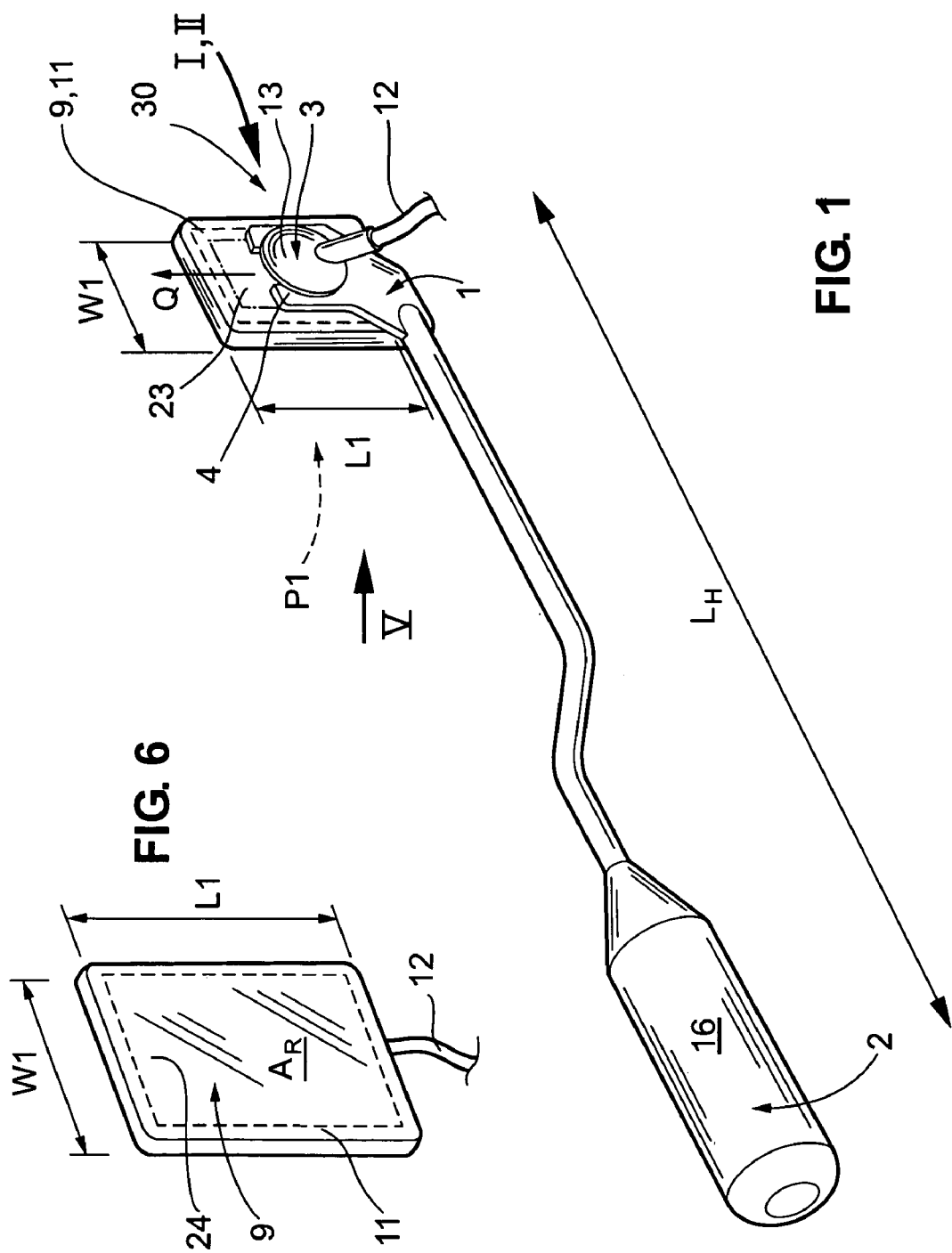
FIG. 1 represents the first embodiment of the inventive arrangement, in which the gap of the holder fork for the neck of sensor peg has a transversal opening direction, the plane of the fork parallel with the length of the holder, the sensor attached in the holder so that it is in the first of its alternative positions, and the other end with a hand grip, in an axonometric view.

The figures show generally an arrangement 30 for connecting a dental X-ray imaging sensor 9 to a holder 8. The dental X-ray imaging sensor 9 is e.g. a CCD-sensor or a CMOS-sensor or any other known or new type of sensor, which is capable to receive the various intensity levels of the X-ray radiation coming through a dental area of a patient, and so forming an image of the radiated dental area, and is capable to transform this dental X-ray image to electrical signals and, accordingly, to electrical data that can be forwarded to further use like visualizing on a display, to be printed or some other means. The possible uses of the images are familiar to persons skilled in the art, and are not explained in detail.

This kind of dental X-ray imaging sensor 9 is a flat piece 11 with a length L1 and a width W1, and a radiation sensitive area $A_R$ extending along and inside the length and the width. The radiation sensitive area $A_R$ is typically planar and contains image pixels receiving the various X-ray radiation intensities and for transforming the radiation image to electrical image data. The flatness of the piece 11 is parallel to the planar sensitive area $A_R$ forming a sensor plane 24. There is also at least one communication line 12 connected to the radiation sensitive area transferring electrical image data from the sensor to the processing unit, not shown in the figures, which is used for display and/or printing and/or storing of the image data, as is generally known. The communication line 12 can comprise electrical wires and/or optical fibers, i.e. this line can be one or several cables, or optical or radiowave transmitter-receiver-system.

The sensor 9 is detachably connected to the holder 8 that is an elongated body having a length $L_H$ and a first end 1 and a second end 2. The first end 1 is provided with means for detachable connection to said sensor, and the sensor 9 is provided with means for its detachable connection to the holder. For this purpose the inventive arrangement comprises a fork 4 in the first end 1 of the holder and a peg 3 in the flat piece 11 of the sensor 9, which peg is adapted to be gripped by the fork.

The peg 3 has a height $H_p$ projecting from the sensor flat piece 11 in a direction perpendicular to its length L1 and width W1, and the peg is provided with a widened outer end 13 and a neck 5 between the widened outer end 13 and the flat piece 11. The neck has a special configuration so that it has a plurality of alternate larger diameters D1 and smaller diameters D2 in a plane perpendicular to the height $H_p$ thereof. These alternating diameters D1, D2, D1, D2 . . . are effective along the circumference of the neck and in plane perpendicular to the height $H_p$ of the peg. In the preferred embodiment, visualized in FIGS. 4A and 4B, the neck 5 is a polygon with at least two pairs of opposite sides 7a and 7b, 7c and 7d having the smaller diameter D2 between the opposite sides. The opposite sides 7a and 7b of the first pair are parallel in respect to each other, and the opposite sides 7c and 7d of the second pair are also parallel in respect to each other. Typically the parallel opposite sides 7a and 7b of the first pair of sides are parallel to the length L1 of the sensor 9 flat piece 11, and the parallel opposite sides 7c and 7d of the second pair of sides are parallel to the width W1 of the flat piece 11 of the sensor 9. The configuration of the neck 5 is symmetrical in respect to a center line C of the neck perpendicular to the length L1 and width W1 of the sensor, which center line is of course parallel to the height $H_p$ of the peg 3. In this embodiment the cross-section of the neck 5 is square, which allows connection of the sensor into the fork in two positions that are perpendicular to each other. When the sides 7a to 7d of the neck are parallel to the length and to the width of the sensor, respectively and the inner walls 17a, 17b of branches of the fork 4 are either parallel or perpendicular to the length $L_H$ of the holder, one of the sensor positions is longitudinal and the other of the sensor positions is perpendicular to the length of the holder. In an alternative embodiment, visualized in FIGS. 5A and 5B, the neck 5 has a plurality of longitudinal ridges 15 forming the larger diameters D1 alternating with the smaller diameters D2 along the circumference. Here too, the configuration of the neck 5 is substantially symmetrical in respect to a center line C of the neck, depending on the number of ridges. This latter embodiment allows connection of the sensor into the fork in a plurality of positions that can have different angles between each other, i.e. both longitudinal and perpendicular to the length of the holder, but also intermediate positions are possible.

The fork 4 at the first end 1 of the holder has a gap 6 that is adapted to fit onto said neck at least in two different positions P1, P2. In the preferred embodiment, visualized in FIGS. 4A and 4B, the gap 6 of the fork 4 has even parallel inner walls 17a, 17b with a spacing D3 therebetween equal to said smaller diameter D2 between the sides of the neck. As can be understood the fork 4 has two branches 20a and 20b and the gap 6 between these branches. In practice the spacing D3 might be slightly smaller than the smaller diameter D2 while the fork 4 is made of a resilient material, whereupon the fork's two branches 20a, 20b grip the neck through their springy action against the opposite sides 7a and 7b, 7c and 7d of the neck ensuring a tight fitting between the peg and the fork. An unintentional loosening of the peg and the sensor is hereby prohibited. In an alternative embodiment, visualized in FIGS. 5A and 5B, the gap 6 of the fork 4 has such opposite inner walls 17a and 17b of the two branches 20a and 20b, which are provided with teeth 21 and which are generally parallel with a spacing D3 therebetween equal to said smaller diameter D2 of the neck. More precisely the spacing D3 in the fork is measured between the tops of the teeth 21. When the fork 4 is made of a resilient material the two branches 20a, 20b grips the neck through their springy action against some opposite sections of the neck. Accordingly, an unintentional loosening of the peg and the sensor is hereby prohibited. As can be understood, the interaction between the fork, more precisely between inner walls 17a and 17b of the two branches 20a and 20b, and the larger and the smaller diameters of the neck 5 prohibits unintended pivot of the sensor 9 in respect to the holder 2 around the center line C.

The neck 5 of the peg 3 has a spacing dimension H1 between the outer end 13 and the flat piece 11 of the sensor, and the fork 4 has a thickness H2 that is at the maximum equal to the spacing dimension H1, but close to it, or thickness H2 is approaching spacing dimension H1, so that the sensor does not substantially tilt in respect to the fork 4. The gap 6 of the fork 4 has an opening direction Q, which can be transversal, as in FIGS. 1 and 3, or longitudinal, as in FIG. 2, to the elongated body of the holder 2, or more precisely transversal or longitudinal in respect to the length $L_H$ of the holder. The fork 4 has a fork plane 23 formed by its branches, and the fork plane 23 is perpendicular to the thickness H2 of the fork.

Figure 3:
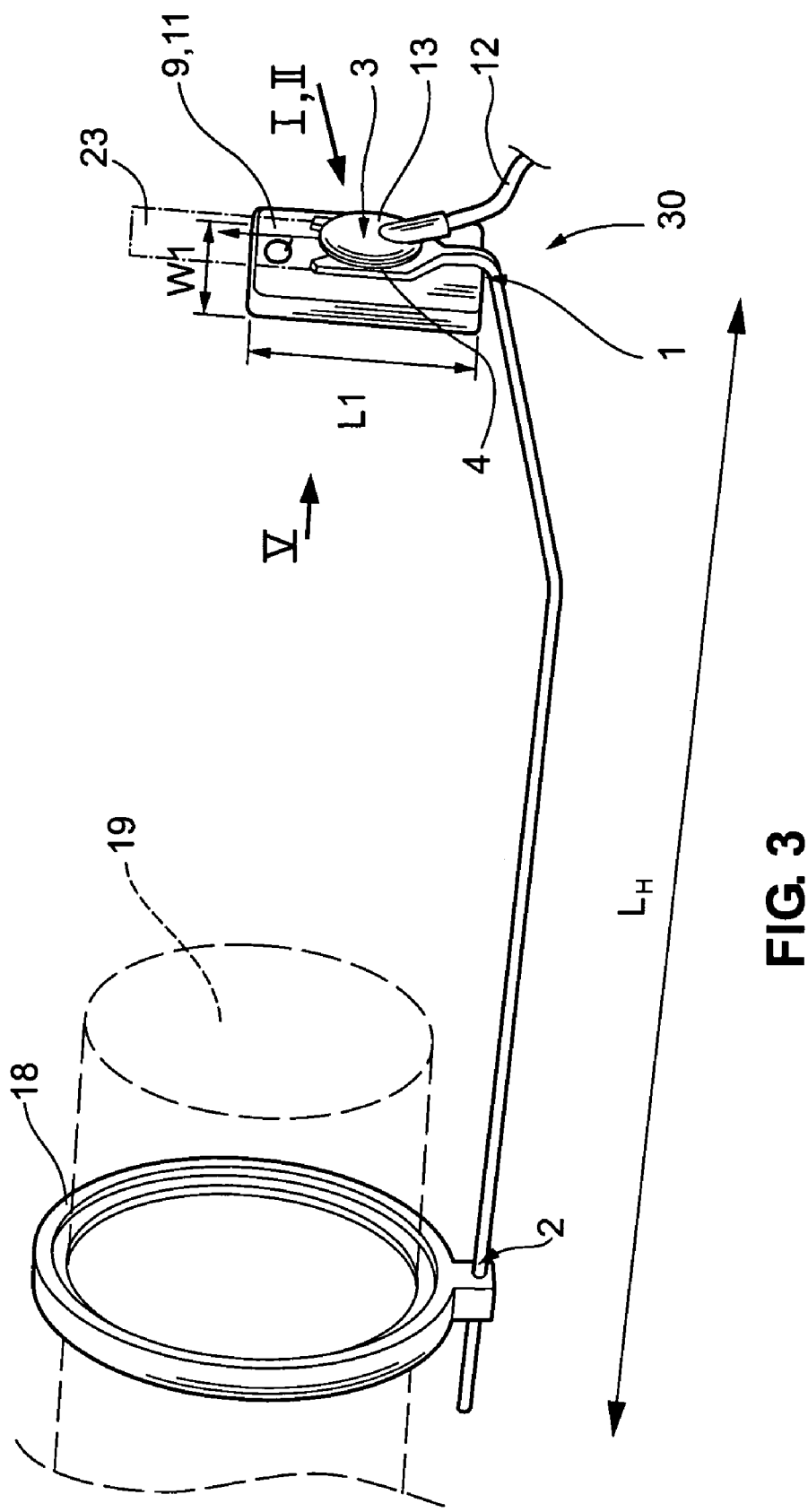
FIG. 3 represents the third embodiment of the inventive arrangement, in which the gap of the holder fork for the neck of sensor peg has a transversal opening direction, the plane of the fork transversal to the length of the holder, the sensor attached in the holder so that it is in the first of its alternative positions, in an axonometric view.

In one alternative embodiment the second end 2 of elongated body of the holder has provisions 16, i.e. a handle 16, for gripping by a person, as shown in FIG. 1. In this case the patient, whose dental area is X-ray photographed keeps the holder in his/hers hand, and the first end of the holder with the sensor 9 in the correct place inside the patient's mouth. Because of supporting by the patient's hand the fork plane 23 formed by the branches of fork 4, the plane 23 being parallel with the sensor plane 24 of the sensor when installed, is parallel to elongated body of the holder 2 in both alternatives of the opening direction Q of the fork, i.e. the opening direction of the gap can be transversal or longitudinal to said elongated body. In another alternative embodiment the second end 2 of elongated body of the holder has a support ring 18 adapted to fit onto a predetermined extension part 19 in an X-ray radiation source, as shown in FIG. 3. In this case there is no need for the patient to keep the holder, but the X-ray radiation apparatus, shown only schematically in FIG. 3, supports the holder, and the first end of the holder with the sensor 9 in the correct place inside the mouth of the patient. Because of supporting by the X-ray apparatus the fork plane 23 formed by the branches of fork 4, the plane 23 being parallel with the sensor plane 24 of the sensor when installed, is transversal to the elongated body of the holder 2 while the opening direction Q of the fork is transversal to said elongated body.

Figure 2:
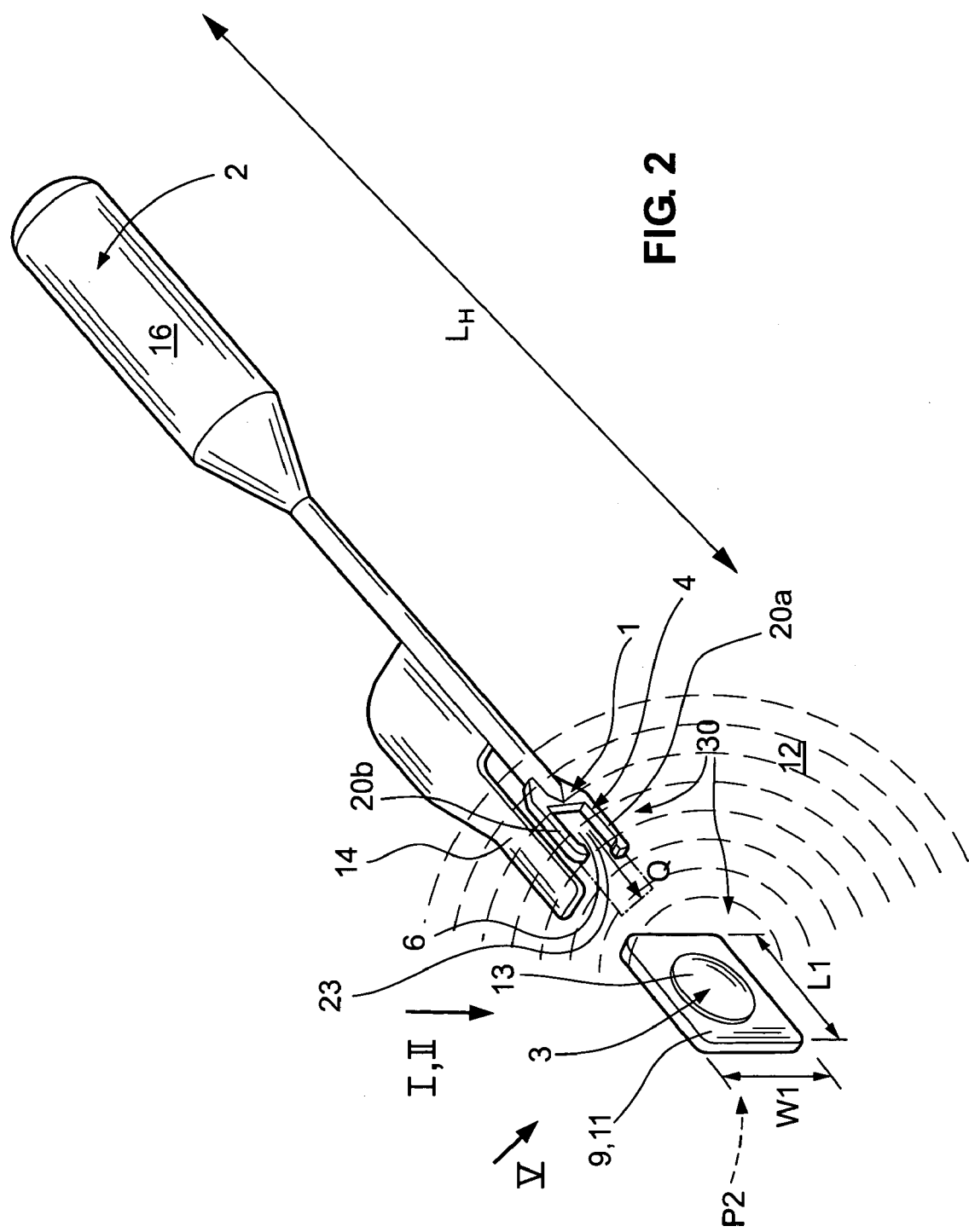
FIG. 2 represents the second embodiment of the inventive arrangement further provided with the bite wing, in which arrangement the gap of the holder fork for the neck of sensor peg has a longitudinal opening direction, the plane of the fork parallel with the length of the holder, the sensor detached from the holder but in the second of its alternative positions, and the other end with a hand grip, in an axonometric view.

Typically the fork 4 is a fixed part of said holder 8 as shown in the figures. The holder can further comprise a bite wing 14 permanently attached to said elongated body of the holder 8, as shown in FIG. 2, which bite wing 14 is to be inserted between and to be bitten by the upper and lower teeth of the patient.

What is claimed is:

1. An arrangement for connecting a dental X-ray imaging sensor to a holder;

said sensor being a flat piece with a length and a width, a radiation sensitive area extending along said length and width, and at least one communication line connected to said radiation sensitive area for data transfer;

said holder being an elongated body having a first end provided with means for detachable connection of said sensor;

said arrangement further comprising:

a peg projecting from said flat piece in a direction perpendicular to said length and width, said peg provided with a widened outer end and a neck between said outer end and said flat piece, said neck having a cross-section with a plurality of alternate larger diameters and smaller diameters; and a fork with a gap at said first end of the holder, said gap being adapted to fit onto said neck at least in two different positions, an interaction between said fork and said larger and smaller diameters of the neck prohibiting unintended pivot of said sensor in respect to the holder.

2. An arrangement of claim 1, wherein said cross-section of the neck is a polygon with at least two pairs of opposite sides having said smaller diameter therebetween.

3. An arrangement of claim 2, wherein said opposite sides of the neck are parallel.

4. An arrangement of claim 3, wherein said cross-section of the neck is symmetrical in respect to a center line perpendicular to said length and width of the sensor.

5. An arrangement of claim 3, wherein said parallel opposite sides of a first pair of sides are parallel to said length of the sensor, and said parallel opposite sides of a second pair of sides are parallel to said width of the sensor.

6. An arrangement of claim 2, wherein said gap of the fork has even parallel inner walls with a spacing therebetween substantially equal to said smaller diameter between the sides of the neck.

7. An arrangement of claim 1, wherein said cross-section of the neck has a plurality of longitudinal ridges.

8. An arrangement of claim 7, wherein said gap of the fork has opposite inner walls, which are provided with teeth and are generally parallel.

9. An arrangement of claim 1, wherein said neck has a spacing dimension between said outer end and said flat piece, and said fork has a thickness at the maximum equal to said spacing dimension.

10. An arrangement of claim 1, wherein said gap of the fork has an opening direction, which is transversal or longitudinal to said elongated body of the holder.

11. An arrangement of claim 10, said opening direction of the gap being transversal to said elongated body of the holder, and a plane of said fork being transversal to said elongated body of the holder.

12. An arrangement of claim 10, said opening direction of the gap being transversal or longitudinal to said elongated body of the holder, and a plane of said fork being parallel to said elongated body of the holder.

13. An arrangement of claim 1, wherein said fork is a fixed part of said holder.

14. An arrangement of claim 1, further comprising a bite wing permanently attached to said elongated body of the holder.

15. An arrangement of claim 1, wherein said elongated body of the holder has a second end with provisions for gripping by a person.

16. An arrangement of claim 15, said opening direction of the gap being transversal or longitudinal to said elongated body of the holder, and a plane of said fork being parallel to said elongated body of the holder.

17. An arrangement of claim 1, wherein said elongated body of the holder has a second end with a support ring adapted to fit onto a predetermined extension part in an X-ray radiation source.

18. An arrangement of claim 17, said opening direction of the gap being transversal to said elongated body of the holder, and a plane of said fork being transversal to said elongated body of the holder.

* * * * *